US00PP25428P3

(12) United States Plant Patent
Egger

(10) Patent No.: US PP25,428 P3
(45) Date of Patent: Apr. 7, 2015

(54) ***HEUCHERA* PLANT NAMED 'ZIPPER'**

(50) Latin Name: ***Heuchera* hybrid**
Varietal Denomination: Zipper

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 83 days.

(21) Appl. No.: 13/987,219

(22) Filed: Jul. 12, 2013

(65) Prior Publication Data

US 2015/0020278 P1 Jan. 15, 2015

(51) Int. Cl.
*A01H 5/00* (2006.01)

(52) U.S. Cl.
USPC ..... Plt./440

(58) Field of Classification Search
CPC ..... A01H 5/00
USPC ..... Plt./440
See application file for complete search history.

*Primary Examiner* — Susan McCormick Ewoldt
*Assistant Examiner* — Keith Robinson
(74) *Attorney, Agent, or Firm* — Klarquist Sparkman, LLP

(57) ABSTRACT

A new and distinct *Heuchera* plant substantially as shown and described, characterized by large, glossy, very ruffled, golden amber to orange leaves, a medium plant size, insignificant flowers in spring, and good vigor.

2 Drawing Sheets

Botanical denomination: *Heuchera* hybrid.
Variety designation: 'Zipper'.

BACKGROUND OF THE INVENTION

The present invention relates to a new and distinct cultivar of *Heuchera* and given the cultivar name of 'Zipper'. *Heuchera* is in the family Saxifragaceae. *Heuchera* 'Zipper' originated from a planned cross between *Heuchera* 'K580-8', a proprietary unreleased, unpatented plant, as the seed parent, and *Heuchera* '148' as the unpatented pollen parent. Compared to the seed parent, *Heuchera* 'K580-8', the new cultivar has amber rather than blue green foliage and insignificant flowers rather than pinkish white flowers. Compared to the pollen parent, *Heuchera* '148', the new cultivar has leaves that are larger, more ruffled, and more brightly colored.

Compared to *Heuchera* 'Marmalade' (US Plant Pat. No. 15,945), the new cultivar has a smaller tighter habit, larger leaves that are more ruffled, glossy rather than matte, and holds the orange gold color all year rather than just orange in the spring.

Compared to *Heuchera* 'Black Taffeta', U.S. Plant patent application Ser. No. 13/987,220, the new cultivar has a smaller habit and foliage color that is golden amber to orange rather than red brown to almost black.

This new *Heuchera* is distinguished by:

1. large, glossy, very ruffled, golden amber to orange leaves,
2. a medium plant size,
3. insignificant flowers in spring on short peduncles, and
4. good vigor.

This new cultivar has been reproduced only by asexual propagation (cuttings and tissue culture). Each of the progeny exhibits identical characteristics to the original plant. Asexual propagation in 2011 by stem cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows an 18 month-old *Heuchera* 'Zipper' growing in part sun in June in Canby, Oreg.

FIG. 2 shows a close up of the flowers of *Heuchera* 'Zipper' in May in Canby, Oreg.

FIG. 3 shows a 10 month old *Heuchera* 'Zipper' in the trial bed growing in full sun in November in Canby, Oreg.

DETAILED PLANT DESCRIPTION

The following is a detailed description of the new *Heuchera* cultivar based on observations of 18 month-old specimens grown in the ground in the trial bed in shade in May in Canby, Oreg. Canby is Zone 8 on the USDA Hardiness map. Temperatures range from a high of 95° F. in August to an average of 32° in January. Normal rainfall in Canby is 42.8 inches per year. The color descriptions are all based on The Royal Horticultural Society Colour Chart, 5$^{th}$ edition, 2007.

Plant:

*Form*.—Basal rosette, herbaceous perennial.
*Hardiness*.—USDA Zone 4 to 9.
*Size*.—27 cm tall from top of the foliage to the ground and 36 cm wide.
*Habit*.—Mounding.
*Vigor*.—Excellent.
*Roots*.—Fibrous, freely branching, fine, and White 155A in color; roots develop easily from stem cuttings.

Leaf:

*Type*.—Simple.
*Arrangement*.—Basal.
*Shape*.—Broadly ovate to orbicular.

*Lobing/division.*—5 main lobes, medium to deeply cut, with 3 to 5 shallow secondary lobes.
*Venation.*—Palmate.
*Margins.*—Deeply crenate and with medium undulation.
*Apex.*—Mucronulate.
*Base.*—Cordate, lobes overlapping slightly at the base.
*Blade size.*—Grows to 11 cm long and 11 cm wide.
*Surface texture.*—Both sides with glandular hairs, topside strongly glossy.
*Petiole description.*—Grows to 18 cm long and 2.5 mm wide, with glandular hairs, Greyed Orange 165A.
*Leaf color.*—Spring topside closest to Greyed Orange 167A with veins Greyed Red 182A at base to Greyed Orange 166D, bottom side and top side edges Greyed Red 181A; summer through winter topside Greyed Orange 174A later lightening to Greyed Yellow 164B, bottom side Greyed Red 181A.

Inflorescence:
*Size.*—Grows to 5 cm wide and 18 cm long.
*Type.*—Upright thyrse.
*Number of flowers per thyrse.*—100 to 160 per thyrse.
*Number of thyrse.*—About 6 in spring bloom.
*Peduncle.*—Grows to 35.5 cm tall, 6 mm wide at base, Greyed Purple 183A, glandular hairs, with 4 to 9 petiolate leaves (ovate, blades grow to 9 cm long and 8 cm wide, 5 to 8 lobed, margin biserrate, topside Greyed Orange 165C with margins Greyed Purple 183A, bottom side Greyed Orange 165C tinted Greyed Purple 183A, margins Greyed Purple 183A; petioles to 13.5 cm long, with glandular hairs, Greyed Orange 165A).
*Pedicel.*—1 mm to 4 mm long, with glandular hairs, Yellow Green 145D in shade and Greyed Red 181B in sun.
*Bloom period.*—May in Canby, Oreg.

Flower bud:
*Size.*—2 mm wide and 3 mm long.
*Description.*—Glandular puberulent, ovoid.
*Color.*—Greyed Orange 166B.

Flower:
*Type.*—Perfect.
*Attitude.*—Side to down-facing.
*Shape.*—Campanulate.
*Size.*—7 mm long and 7 mm wide.
*Petal description.*—5 in number, 4 mm long and less than 1 mm wide, reflexed, spatulate with a clawed base, tip acute, margin entire, glandular hairs on top and bottom, White NN155C on both sides.
*Calyx description.*—3.5 mm long and 4 mm wide, with 5 lobes, widely spaced, divided ½ way to the base, glandular hairs on outside, glabrous inside, tip acute, margin entire, both sides top Yellow Green 147C tinted Greyed Orange 166B.
*Stamen description.*—5 in number, each 2.5 mm long, White NN155C, anthers less than 1 mm, Yellow Orange 21C, no pollen, male sterile.
*Pistil description.*—One central two beaked pistil, 7 mm long, Yellow Green 147C overall, style 5 mm long, ovary 2 mm long.
*Fragrance.*—None.
*Lastingness.*—Each thyrse blooms for about 2 weeks on the plant.

Fruit:
*Type.*—Two-beaked ovoid capsule.
*Description.*—6 mm long and 6 mm wide, glandular puberulent.
*Fertility.*—Low.
*Color.*—Greyed Brown 199C.

Seed: ° x.
*Shape.*—Linear.
*Size.*—2 mm long.
*Color.*—Black 202A.

Disease and pest tolerance: Pest and disease resistance are typical for this type of *Heuchera.*

I claim:

1. A new and distinct *Heuchera* plant as herein illustrated and described.

* * * * *

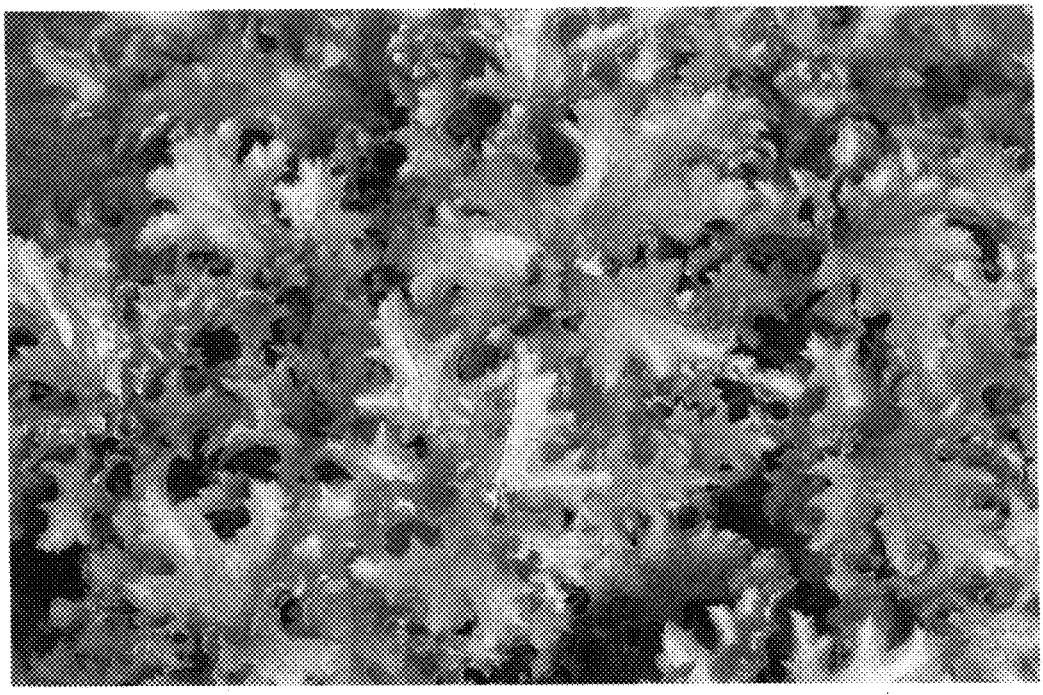
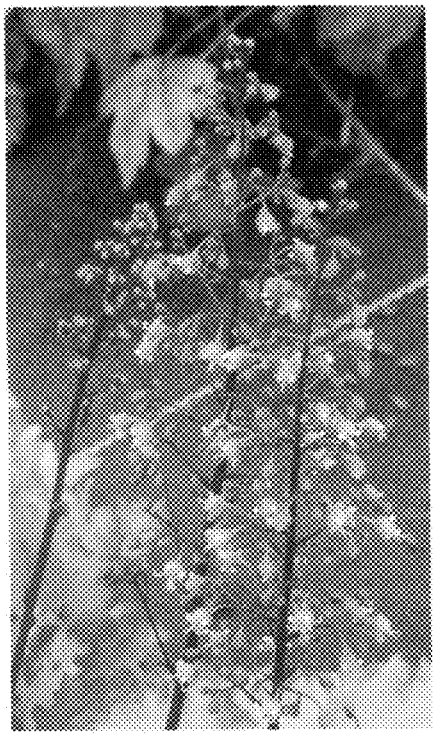
FIG. 1 above
FIG. 2 on left

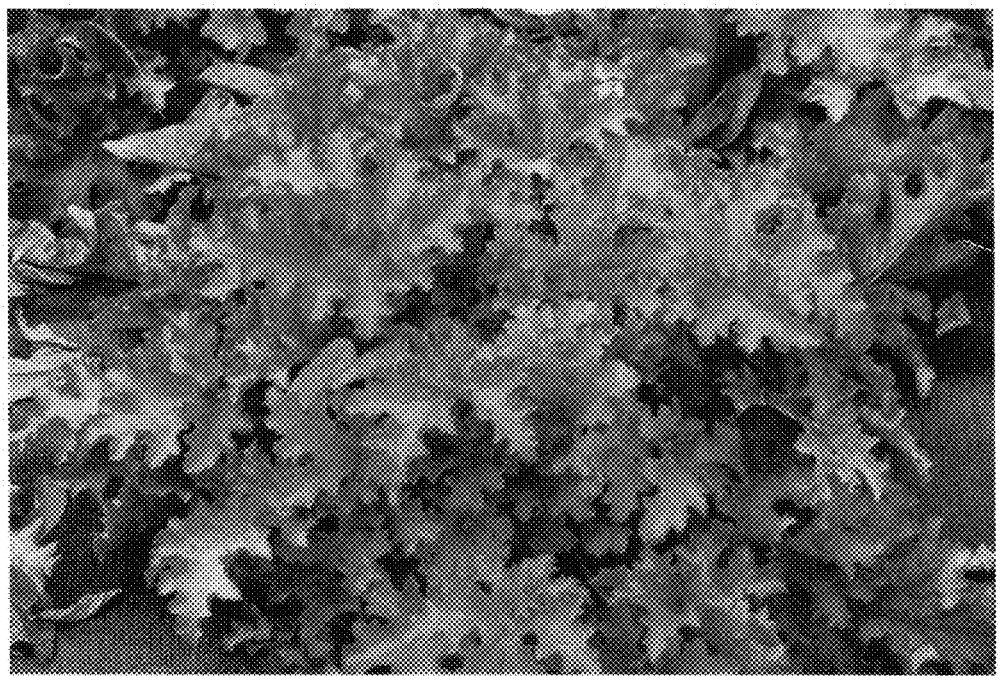
FIG. 3 above